United States Patent [19]

Heine et al.

[11] Patent Number: 4,721,108

[45] Date of Patent: Jan. 26, 1988

[54] GENERATOR FOR A PULSE TRAIN OF SHOCKWAVES

[75] Inventors: Gerold Heine, Oberuhldingen; Othmar Wess, Immenstaad, both of Fed. Rep. of Germany

[73] Assignee: Dornier System GmbH, Friedrichshafen, Fed. Rep. of Germany

[21] Appl. No.: 531,088

[22] Filed: Sep. 12, 1983

[30] Foreign Application Priority Data

Nov. 4, 1982 [DE] Fed. Rep. of Germany ....... 3240691

[51] Int. Cl.[4] .................................... A61B 17/22

[52] U.S. Cl. .................................... 128/328

[58] Field of Search ................. 128/328, 24 A, 419 R, 128/303 R, 804

[56] References Cited

U.S. PATENT DOCUMENTS 2,559,227 7/1951 Reiba ................................ 128/24 A 4,311,147 1/1982 Hausler .............................. 128/328

FOREIGN PATENT DOCUMENTS 2508494 9/1976 Fed. Rep. of Germany ...... 128/804

2913251 10/1980 Fed. Rep. of Germany ...... 128/328

*Primary Examiner*—Lee S. Cohen

*Attorney, Agent, or Firm*—Ralf H. Siegemund

[57] ABSTRACT

A generator for pulse trains of shockwaves for the purpose of contactlessly comminuting concretions in living bodies, comprising a shockwave source, for instance a spark gap, a focusing reflector, for instance a hollow ellipsoid filled with a propagation medium, and a layer of a material having an impedance different from that of the medium of propagation mounted in such a manner that it is crossed by the shockwave field.

12 Claims, 4 Drawing Figures

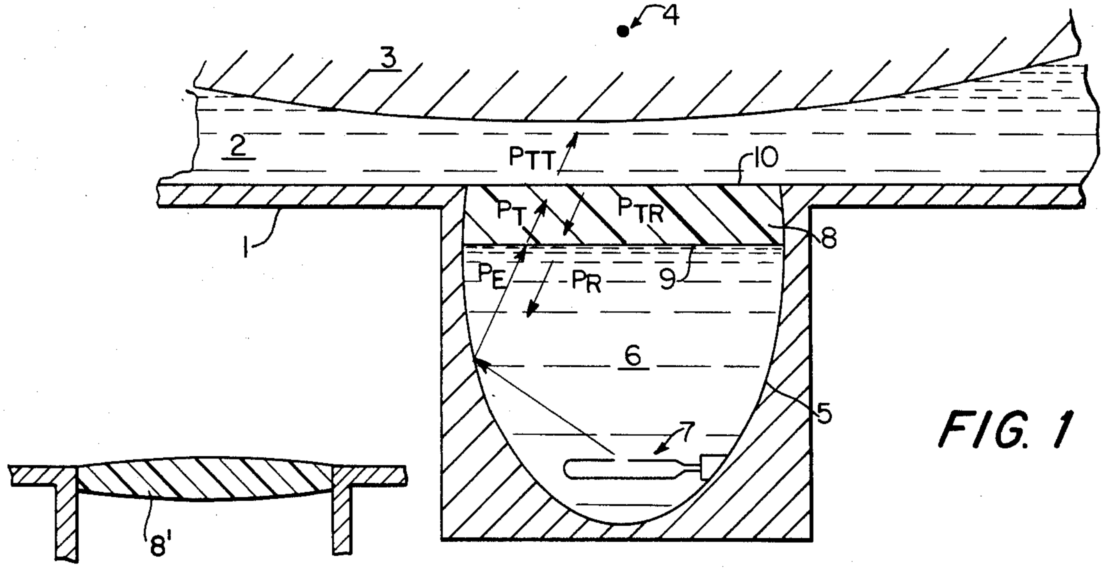
FIG. 1
FIG. 1a
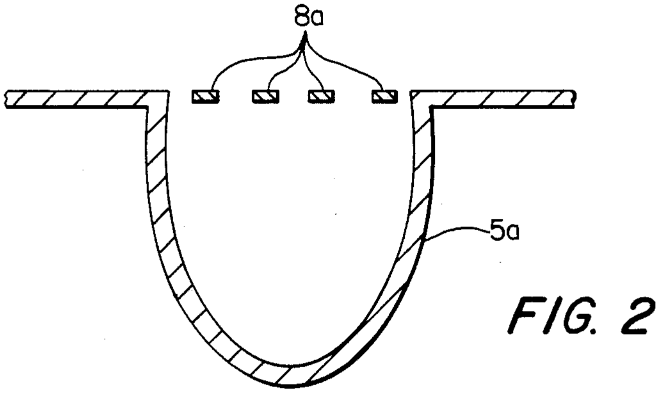
FIG. 2
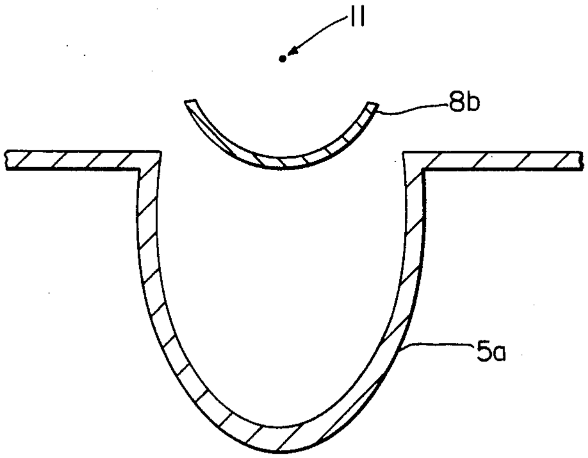
FIG. 3

GENERATOR FOR A PULSE TRAIN OF SHOCKWAVES

BACKGROUND OF THE INVENTION This invention relates to an apparatus for generating a pulse train of shockwaves for the contactless comminution of concretions in living bodies.

U.S. Pat. No. 3,942,531, discloses an apparatus for the contactless comminution of concretions in living bodies using shockwaves. According to this patent, the shockwaves are generated by a spark gap located at one focus of a hollow ellipsoid filled with a liquid, and is focused by the ellipsoidal surface onto the second focus where the concentration to be destroyed, for instance a kidney stone, is located. The shockwaves stress the concretion compressively and tensively and cause parts of the concretion to break off. In the known apparatus, the frequency of the shock sequence is limited by the charging time of the capacitors. Simultaneous treatment of a concretion by two or more shockwaves is impossible with this apparatus.

In order to apply several shockwave fronts approximately simultaneously to a concretion, these fronts must follow each other within 0.1 to 10 microseconds. Attempts already have been made to release double pulses by using two impulse generators, however a time difference of only 20 milliseconds could be achieved. At that time, however, the crack formation initiated by the first shock waves is already terminated.

DESCRIPTION OF THE INVENTION

It is the object of the present invention to provide an apparatus for generating pulse trains of shockwaves for which the shockwave fronts act on the concretion at time intervals so close to each other that the concretion is still being acted on by the first wave front when the subsequent wave front interacts with the concretion, the steepness of the slope of the pressure increase being required to remain undiminished.

This problem is solved by the invention by an apparatus wherein a layer of uniform thickness and made of a material with an impedance different from that of the medium of propagation is so arranged in the propagation medium that it will be crossed by the entire shockwave field.

The basis of the invention is that a single pulse generated by the spark gap is multiplied by multiple reflections at the front and rear sides of a layer with an impedance different from that of the medium of propagation. Thus, in response to and by interaction with a single pulse, the layer generates a plurality of shock waves, i.e. a sequence of tightly following shockwave fronts of the desired pulse repetition frequency. Due to the interactions between various shockwave fronts within the same concretion, interferences are generated which locally increase the amplitudes of compression and tension and excite special resonance frequencies, thereby increasing the effectiveness of comminution. The solution of the invention furthermore offers the advantage that, despite the increased destruction output, the energy fed into the living body is not increased. Thereby injury to the tissue crossed by the shockwave is avoided while the concretions nevertheless are reliably comminuted into small fragments more rapidly than before. Fewer applications are required because of the enhanced comminution effect. The patient is less stressed and the service life of the electrode is increased.

DESCRIPTION OF THE DRAWINGS

The invention will be further illustrated by reference to the accompanying drawings, in which:

FIGS. 1 through 3 show various illustrative embodiments of the invention and wherein FIG. 1*a* illustrates a detailed modification.

FIG. 1 shows an apparatus in accordance with the invention for generating pulse trains of shockwaves. A body 3 with a concretion 4, for instance a kidney stone, is placed in a tub 1 (only partly shown) filled with a liquid 2. An elliptical reflector 5 is mounted to the tube 1 and filled with a coupling liquid 6 (for instance water). A spark gap 7 is positioned at the first focus of the ellipsoid 5 and can produce a shockwave front by discharging.

The body is so positioned that the concretion 4 is located at the second focus of the ellipsoid. In this embodiment, the reflector 5 is provided with a layer 8 according to, the invention. The layer includes the boundary surfaces 9 and 10 but is not shown to scale in FIG. 1. The thickness of actual layers is in the mm range. A submerged discharge is ignited at the spark gap 7 to comminute the concretion 4. This submerged discharge generates a shockwave front spreading at the reflector 5 and is guided and focused by the reflector walls onto the concretion 4. The figure also shows a wave normal of amplitude $P_E$. At the boundary surface 9 the incident wave $P_E$ splits into a transmitted wave $P_T$ and into a reflected wave $P_R$ anytime the layer 8 is of an acoustic impedance $z_8=c_8\cdot\rho_8$ differing from that of the coupling liquid 6 ($z_6=c_6\cdot\rho_6$), where c=speed of sound (for the respective medium and $\rho$ the respective density.

Based on the acoustic relationships, the amplitude of the reflected wave when normally incident is given by $$P_R = P_E \cdot \frac{z_8 - z_6}{z_8 + z_6}$$

and for the transmitted wave it is $$P_T = P_E - P_R = P_E \cdot \left(1 - \frac{z_8 - z_6}{z_8 + z_6}\right)$$

For a thickness d of the layer 8 and for the same impedance of the medium 2 behind it as the medium 6 in front of it, the transmitted wave in turn is split into a transmitted wave $P_{TT}$ and a reflected wave $P_{TR}$ at the time the wave fronts arrive at the rear boundary surface 10 of the layer 8. The amplitudes again can be computed in the same manner as the above formulas. While the wave $P_{TT}$ continues in the original direction, the wave $P_{TR}$ returns into the layer 8 and undergoes an new reflection (with corresponding amplitude attenuation) at the front boundary surface 9. A corresponding fraction of this wave passes through the rear boundary surface 10 and follows the first transmitted wave $P_{TT}$ at a time delay $\Delta t$. $\Delta t$ is the time required to pass twice through the layer thickness d, $$\Delta t = 2d/C_8.$$

Due to multiple reflections at intervals $n\cdot\Delta t$(n=1, 2, . . . ), these and further waves ensue, the amplitudes of the individual waves decreasing geometrically. The parameters ρ, c and d can be widely selected as desired by selecting suitable materials and accordingly the desired pulse repetition frequencies (which for a given selected material depend upon the thickness of the layer 8) and the amplitude ratios (depending upon the magnitude of the impedance step $z_8 - z_6$ and the layer thickness d) can be determined within wide limits.

Experiment has shown that for instance with titanium plates with thicknesses from 0.5 to 3 mm the steepness of the slope of the individual pulses generated by multiple reflections is uniformly high.

A layer of suitable thickness can be made for instance from aluminum, V2A-Steel, titanium, lead or similar materials or alloys thereof and also from suitable non-metals, ceramics or plastics. In some circumstances, certain liquids may be applicable provided they are retained in corresponding shapes, for instance by means of pads.

In addition to the arrangement shown in FIG. 1, wherein the entire shockwave field is constrained to cross the layer, other systems also are feasible to divide up the shockwave front.

FIG. 2 shows an arrangement with a reflector 5*a* wherein the layer 8*a* is in the form of a zone plate. This layer now is crossed only by fractions of the shockwave field. The shockwave portions that do not cross the layer 8*a* arrive unattenuated at a time $t_o$ at the concretion. The remaining shockwave portions undergo multiple reflections and the first pulse of the pulse train arrives at the concretion at time $$t - t_o = (d/c_8) - (d/c_6).$$

By suitably combining the material, layer thickness, and zone sequence in the zone plate, it is possible thereby that for instance the second (third, etc.) pulse of the shockwave train be of the largest amplitude. For $c_8 > c_6$, which is the case for metals for instance, the primary wave can arrive delayed with respect to that crossing the plate.

FIG. 3 shows an arrangement wherein the layer 8*b* of the invention is in the form of a spherical dish mounted concentrically with the focus 11 of the shockwave. All parts of the focused shockwave travel perpendicularly to the layer surface. The conditions of reflection and the time shift Δt of the wave front therefore are constant for all parts of the wave field. Also, the focusing remains therefore unaffected.

Further embodiments of the invention are possible for which the various features shown herein are combined. Again it is possible to use layers lacking uniform thickness, for instance, being lenticularly shaped as shown representatively by the lenticularly shaped layer 8' in FIG. 1*a*.

It will be obvious to those skilled in the art that many modifications may be made within the scope of the present invention without departing from the spirit thereof, and the invention includes all such modifications.

What we claim is:

1. In an apparatus for generating pulse trains of shockwaves for the contactless comminution of concretions in living bodies, comprising a shockwave source including a spark gap, and a reflector for focusing including a hollow ellipsoid filled with a propagation medium, the spark gap being mounted in one focal point of the ellipsoid, the ellipsoid having an opening, the improvement comprising layer means across said opening for generating a plurality of shockwaves having a thickness equal to its propagation speed of sound multiplied by a time period between about 5 and 0.05 microseconds and made from a material having an impedance different from that of the propagation medium, said layer means being mounted in such a manner that it is crossed by the shockwave field, propagation medium being present on opposite sides of the layer means.

2. An apparatus according to claim 1, the layer means being continuous across said opening to be the entire shockwave field.

3. An apparatus according to claim 1, or claim 2, in which the layer means is mounted in a central plane between the one focus and a second focus of the hollow ellipsoid.

4. An apparatus according to claim 1 or claim 2 in which the layer means seals the reflector.

5. An apparatus according to claim 1, the layer means being discontinuous across said opening to be crossed only by portions of the shockwave field.

6. An apparatus according to claim 5, in which the layer means (8*a*) is a zone plate.

7. An apparatus according to claim 1 the layer means being constructed in the form of a spherical dish mounted concentrically with the shock wave fronts.

8. An apparatus according to claim 1, in which metals or alloys are used as the material.

9. An apparatus according to claim 1, in which plastics or ceramic materials are used as the material.

10. An apparatus according to claim 1, in which the layer means is of uniform thickness.

11. An apparatus according to claim 1, in which the thickness of the layer means varies.

12. Apparatus according to claim 1, in which the layer means assumes a lenticular shape.

* * * * *